United States Patent
Sun et al.

(10) Patent No.: US 6,455,058 B1
(45) Date of Patent: Sep. 24, 2002

(54) COMPOSITION AND METHOD FOR HAIR AND SCALP TREATMENT

(75) Inventors: Ziming Sun, Fountain Valley, CA (US); James W. Parr, San Juan Capistrano, CA (US); Darcy Travaline, Coto De Caza, CA (US); Carolina Nguyen, Garden Grove, CA (US)

(73) Assignee: Amitee Cosmetics, Inc., Costa Mesa, CA (US)

( * ) Notice: Subject to any disclaimer, the term of this patent is extended or adjusted under 35 U.S.C. 154(b) by 0 days.

(21) Appl. No.: 09/661,418

(22) Filed: Sep. 13, 2000

(51) Int. Cl.⁷ .............................. A61K 7/00; A61K 7/06; A61K 7/075; A61K 25/00
(52) U.S. Cl. .................. 424/401; 424/70.1; 424/70.11; 424/70.21; 514/852; 514/880; 514/881
(58) Field of Search ................................ 424/401, 70.1, 424/70.11, 70.21, DIG. 4; 514/880, 881, 852

(56) References Cited

U.S. PATENT DOCUMENTS

| | | | |
|---|---|---|---|
| 3,954,113 A | 5/1976 | Bohrer et al. .................. 132/7 |
| 3,980,091 A | 9/1976 | Dasher et al. ................. 132/7 |
| 4,061,150 A | 12/1977 | Dasher et al. ................. 132/7 |
| RE30,874 E | 3/1982 | Dasher et al. ................. 132/7 |
| RE31,126 E | 1/1983 | Dasher et al. ................. 132/7 |
| 4,557,928 A | * 12/1985 | Glover |
| 5,104,645 A | * 4/1992 | Cardin et al. |
| 5,409,640 A | 4/1995 | Giret et al. ................. 252/546 |
| 5,756,080 A | 5/1998 | Janchitraponvej et al. ...................... 424/70.122 |
| 5,776,872 A | 7/1998 | Giret et al. ................. 510/124 |
| 5,858,342 A | 1/1999 | Giret et al. .............. 424/70.19 |
| 5,942,477 A | 8/1999 | Giret et al. ................. 510/124 |
| 5,942,479 A | 8/1999 | Frankenbach et al. ...... 510/159 |
| 5,968,491 A | 10/1999 | Richardson ................ 424/70.1 |
| 5,977,037 A | 11/1999 | Giret et al. ................. 510/122 |
| 5,985,809 A | 11/1999 | Frankenbach et al. ...... 510/159 |
| 5,994,280 A | 11/1999 | Giret et al. ................. 510/130 |
| 6,004,915 A | 12/1999 | Elliott et al. ................ 510/135 |
| 6,010,690 A | 1/2000 | Varco ...................... 424/70.13 |
| 6,013,250 A | 1/2000 | Cannell et al. .......... 424/70.51 |
| 6,033,652 A | 3/2000 | Ansmann ............... 424/70.122 |
| 6,048,520 A | 4/2000 | Hoshowski .............. 424/70.17 |

FOREIGN PATENT DOCUMENTS

| WO | WO 98/23258 | 6/1998 |
|---|---|---|
| WO | WO 99/27900 | 6/1999 |

OTHER PUBLICATIONS

Department of Health and Human Services Food and Drug Administration, Agency: Food and Drug Administration, HHS, 21 CFR Parts 310 and 358, Dandruff, Seborrheic Dematitis, and Psoriasis drug Products for Over–the–Counter Human Use; Final Monograph [Docket No. 82N–0214] RIN 0905–AA06; 56 FR 63554; Dec. 4, 1991 vol. 56, No. 233, pp. 63568–63569.

* cited by examiner

*Primary Examiner*—Thurman K. Page
*Assistant Examiner*—S. Tran
(74) *Attorney, Agent, or Firm*—Jeffer, Mangels, Butler & Marmaro LLP

(57) ABSTRACT

A hair and scalp treatment composition containing (1) an anti-dandruff agent such as salicylic acid, (2) a polyethylenimine, and (3) an amphoteric surfactant. The composition provides superior effects for repairing damaged hair, protecting hair against chemical and mechanical damage. In addition, the composition also provides scalp treatment for against dandruff, seborrheic dermatitis and psoriasis. The composition could be incorporated into either aqueous or anhydrous solvent systems.

1 Claim, No Drawings

COMPOSITION AND METHOD FOR HAIR AND SCALP TREATMENT

FIELD OF THE INVENTION

This invention is directed to the field of hair and scalp treatments.

BACKGROUND OF THE INVENTION

The following is intended to provide a background of the inventive composition and method of this patent; however, this discussion is not intended to suggest that the information set forth is prior art.

In today's hair care market, there continues to be a long-felt need for hair care products effective to facilitate the prevention of hair damage and also to repair damaged hair. There are many different products in the market and most of them target specific problems. Since most people have an accelerated life pace, they are looking for multi-functional products that can simplify their daily routine.

Pre-shampooing hair treatment or conditioning formulas are different from regular conditioners or conditioning rinses. In general they have stronger conditioning ingredients that are substantive to hair and will be left on the hair after shampooing. Upon rinsing the treated hair, the conditioning ingredients will be deposited on hair evenly to give hair softness and/or smoothness of feel, luster, body as well as manageability. For example, polyethylenimine (PEI) has been used in pre-shampooing condition treatments for this purpose. In comparison, regular conditioners or conditioning rinses generally do not leave a deposit on the hair for an appreciable length of time after rinsing, because of the small molecular weight of the conditioning ingredients.

Water-soluble cationic surfactants and PEI are cationic conditioning ingredients. Water-soluble cationic surfactants are widely used in after shampooing conditioners or conditioning rinses. In contrast, PEI has not been a widely used ingredient in after shampooing conditioners or conditioning rinses. If PEI is used in after shampooing conditioners or conditioning rinses, two problems are usually encountered: (1) over build-up of cationic polymer and (2) the hair has an unpleasant after-feel. When PEI is used in a pre-shampoo conditioning treatment, shampooing will remove the PEI polymer and cationic surfactants that have less affinity for the hair so there is less build-up. The leftover PEI polymer is evenly distributed on the hair and therefore leaves the hair soft and smooth with increased luster and manageability. Since PEI is a cross-linking polymer with a very high cationic charge density, it will coat the hair shaft very well, which will help repair split-ends as well as other chemical and mechanical damage to the hair. In addition, the cationic polymer can form stronger hydrogen bonds with hair and water in order to help balance the moisture content of hair.

PEI however is incompatible with many anionic surfactants in shampoo formulations in the normal pH range of shampoo, namely, 2 to 9. Indeed, mixing PEI with sodium lauryl sulfate forms a precipitate in the pH range of 2 to 9.

There are a number of chemicals useful as anti-dandruff agents. For example, zinc pyrithione and salicylic acid have been approved by the Federal Drug Administration for use as an anti-dandruff, anti-seborrheic dermatitis, and anti-psoriasis, ingredient in shampoos and skin care products for over the counter applications. There are various shampoos and body wash products in the market containing salicylic acid that target scalp and skin problems.

It is apparent that if one could use an anti-dandruff agent such as salicylic acid in the regular formula of conditioning rinses or leave-in conditioners as a scalp treatment ingredient, these products would have dual functions: (1) scalp treatment and (2) hair conditioning. Unfortunately, an agent such as salicylic acid is incompatible with cationic ingredients in conditioning rinses or in leave-in conditioners. Therefore, the most popular treatment compositions combine salicylic acid and anionic surfactants in cleansing formulations or use salicylic acid in emulsions.

Thus there exists a long felt, but unsolved need, for a composition for both hair and scalp treatment.

SUMMARY OF THE PREFERRED EMBODIMENTS

The present invention solves the foregoing need. The inventive composition utilizes, preferably, polyethylenimine (PEI) and an anti-dandruff agent in one formula so as to have both hair and scalp treatment functions. In general, the anti-dandruff agents are those that are incompatible with cationic ingredients in conditioning rinses or in leave-in conditioners. Preferably, the anti-dandruff agents are selected from the group consisting of salicylic acid, zinc pyrithione and mixtures thereof. The combination of PEI and the anti-dandruff agent can be incorporated into both the aqueous phase and the anhydrous phase.

In general, the inventive composition is composed of two major ingredients: polyethylenimine and/or its derivatives and mixtures thereof (individually and collectively "PEI") and the foregoing anti-dandruff agents, preferably salicylic acid. Preferably, the composition includes: polyethylenimine in the amount of about 0.01% to about 8.0% and the anti-dandruff agent in the amount of about 0.01% to about 7.0% by total weight of the composition.

PEI are molecules with the units $[(CH_2CH_2NH)_n]$ of ethylenimine ranging from preferably 7 to 14,000 units with a corresponding molecular weight in the range of 300 to 602,000. Polyethylenimine has a three-dimensional cross-linking structure and is able to "wrap" or "coat" hair to form an even film. To activate the conditioning function of polyethylenimine, neutralization is needed and the following three neutralizers are preferred: lactic acid, glycolic acid and benzoic acid. The amount of these acids depends upon the amount of polyethylenimine and the molecular weight of these three acids.

Preferably, the anti-dandruff agent is in the amount of about 0.01% to about 8.0% by total weight of the composition. In the composition of the present invention, this agent is neutralized to the pH range for regular cosmetic products with organic amines before mixing it with neutralized PEI. The amount of organic amines depends upon the amount of the agent and also the molecular weight of the organic amines.

Amphoteric surfactants (for example, alkyl betaines, alkylamido betaines, acylamphoglycinate and acylamphoproplonates) can also be used in the inventive composition. The amount of amphoteric surfactants preferably ranges from about 0.01% to about 12.0% of the total weight of the composition. Other ingredients can include preservatives, fragrance, de-ionized water and/or other organic solvents.

The effective preferable pH range of the inventive composition is in the range of about 2 to about 9 for aqueous based formulas. To exert the self-heating "hot oil" function, lower molecular weight glycols and/or polyethylene glycols are used as solvents to replace deionized water. Examples of these glycols include propylene glycol, glycerin, polyethylene glycol 4–12, polypropylene glycol 7–15 and tripropylene glycol methyl ether. The ratio of PEI and anti-dandruff agents as well as all neutralization ingredients are kept the same as in the aqueous formula.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

The inventive treatment composition contains a highly cationic polyethylenimine (PEI), a very effective hair conditioning ingredient, generally in the amount of about 0.01% to about 8.0%, preferably in the amount of about 0.10% to about 6.0%, and more preferably in the amount of about 0.5% to about 5.0%, by total weight of the composition, and an anti-dandruff agent, generally in the amount of about 0.01% to about 7.0%, preferably in the amount of about 0.10% to about 5.0%, and more preferably in the amount of about 0.5% to about 4.0%, by total weight of the composition. If zinc pyrithione is used as the anti-dandruff agent, the most preferable range is 0.1% to 3.0% of the total weight of the composition. The composition can also include amphoteric surfactants generally in the amount of about 0.01% to about 12.0%, preferably in the amount of about 0.10% to about 9.0%, and more preferably in the amount of about 0.5% to about 6.0%, by total weight of the composition. To help activate polyethylenimine, an acid, preferably lactic acid, glycolic acid and/or benzoic acid, are employed in the amount of about 0.2% to about 6.5% by total weight of composition depending on the molecular weight of the acid.

Water-soluble organic amines can be used to neutralize the anti-dandruff agent in the range of about 0.01% to about 10.0%, preferably about 0.10% to about 6.5%, and more preferably about 0.05% to about 5.0%, of the total weight of the composition depending on the molecular weight of the amines. Other ingredients that can be used in the composition are fragrance, preservatives and solvents (water or organic solvents). Exemplar preservatives include methylparaben, propylparaben, and DMDM hydantoin and exemplar organic solvents include propylene glycol, glycerin, polyethylene glycol 4–12, polypropylene glycol 7–15, and tripropylene glycol methyl ether.

The inventive pre-shampooing hair treatment provides the hair with improved physical and cosmetic conditioning properties for instant thickness, softness, gloss and manageability, including excellent wet and dry combing and body. In addition, it also provides scalp-conditioning benefits to fight against dandruff, seborrheic dermatitis and psoriasis. It is a helpful product for people who have dandruff, seborrheic dermatitis and psoriasis, among other scalp problems. They do not have to use anti-dandruff, anti-seborrheic dermatitis and psoriasis products daily and separately. Thus the composition of the present invention will help decrease the itchiness of the scalp.

The polyethylenimines used in the hair treatment composition should be both water soluble or soluble after neutralization and/or organic solvent soluble (lower molecular weight glycols and/or polyethylene glycols). The suitable polyethylenimines include, but are not limited to, molecules in the classes known as polyethylenimine, hydroxyethyl polyethylenimine, graft copolymers of polyethylenimine and silicone polymers.

The performance of the inventive composition is in part directly related to the molecular weight or structure of the polyethylenimines. In terms of conditioning properties, in general, the larger or longer chain the polyethylenimine molecule is, the better performance one obtains. However, if the molecule is too large, it may be difficult to remove it from the hair by shampooing. The suitable sizes of molecular weight are generally in the range of 300 to 602,000, preferably in the range of 645 to 107,500, and more preferably in the range of 1300 to 75,250. A range of 300 to 602,000 corresponds to the units of ethylenimine, which range from 7 to 14,000 $\{(CH_2CH_2NH)_n, n=7–14,000)\}$. The more preferable range of from 30 to 1,750 units corresponds to a molecular weight range of 1300 to 75,250.

In general the pH should range from 2.0 to 9.0, preferably from 2.5 to 8.0, and the most effective performance pH range of polyethylenimines is between 3.0–7.0. Therefore, an acid is used to neutralize the PEI component of the composition of the present invention. Lactic acid, benzoic acid and/or glycolic acid have been preferably chosen to neutralize polyethylenimine to decrease the pH to 2–9. Other acceptable acids include acetic acid and propionic acid. Acetic acid and propionic acid can be used as neutralizers, but the odor of both ingredients are difficult to mask. Most inorganic monoacids can be used to play the same function. However, in general, inorganic multiple-acids and organic multiple acids (e.g. citric acid) are not suitable for neutralization function and they would have an incompatibility problem with polyethylenimines. Inorganic monoacids that are satisfactory include hydrochloride acid, hydrobromide acid and nitric acid.

The polyethylenimine and/or its derivatives used in the inventive composition include, but not limited to, Hydroxyethyl PEI-1000, Hydroxyethyl PEI-1500, Polyethylenimine7, Polyethylenimine 10, Polyethylenimine 15, Polyethylenimine 30, Polyethylenimine 35, Polyethylenimine 45, Polyethylenimine 250, Polyethylenimine 275, Polyethylenimine 700, Polyethylenimine 1000, Polyethylenimine 1400, Polyethylenimine 1500, Polyethylenimine 1750, Polyethylenimine 2500, Polyethylenimine 14000, and various Polyethylenimine-silicone graft copolymers.

The benefits of using polyethylenimine and its derivatives in hair conditioning originate from the three-dimensional cross-linking structures of polyethylenimine and/or its derivatives. After neutralized to pH at 2–9, polyethylenimines become highly positive charged polyethylenimonium. Neutralized polyethylenimonium generally readily deposits on hair since natural hair usually carries some anionic charge. These cross-linking molecules can tightly "coat" the hair surface. Shampooing only removes the loosely deposited part and leaves the "left over" part evenly spread on the hair. It gives hair softness, smoothness, gloss, moisture and manageability.

In order to link scalp treatment together with hair treatment in the same product, an anti-dandruff agent such as salicylic acid has been incorporated into the composition. Salicylic acid has been approved by Federal Drug Administration as an anti-dandruff, anti-seborrheic dermatitis and anti-psoriasis ingredient in over the counter products.

The inventive composition starts with two separated phases: one bears neutralized polyethylenimonium and the other contains neutralized anti-dandruff agent such as salicylic acid at about the same pH. By using amphoteric surfactants in either one of two water phases, physical and chemical stable composition have been obtained.

In general, it is important to control the ratio of the anti-dandruff agent to the PEI because of the potential incompatibility between these two ingredients. In general, the ratio of the salicylic acid to the PEI should range from about 1.0:0.05 to about 1.0:50, preferably from about 1.0:0.07 to about 1.0:35, and more preferably from about 1.0:0.1 to about 1.0:20. By employing these ratios, the resulting composition is stable after customary thermal and physical tests. Those tests include three cycle freeze and thaw, and elevated temperature at 40° C. and room temperature stability. By stable, it is meant that the composition solution did not materially change and there is not any significant phase separation as well as significant precipitation.

Suitable organic amines include, but not limited to, primary amines ($RNH_2$), secondary amines ($R_2NH$) and tertiary amines ($R_3N$). Within this class of amines, the most effective molecular weight range is from 100 to 2,000, although the preferable range is from 100 to 1500 and more preferably from 100 to 1000. The R groups include but are not limited to Alkyl, Aryl, Alkylamidopropyl, Polyethylene (and/or polypropylene), Glycol Alkyl, Hydrogenated Tallow, and Polyethylene Glycol Hydrogenated Tallow. Alkyl groups could be linear or branched and Aryl groups could be Aryl derivatives.

Examples of organic amines include, but not limited to, Babassuamidopropyl Dimethylamine, Behenamidopropyl Dimethylamine, Diethanolamine, Almondamidopropyl Dimethylamine, Cocamidopropyl Dimethylamine, Aminopropyl Laurylglutamine, Cocamine, Cocoyl Polyglyceryl-4 Hydroxypropyl Dihydroxyethylamine, Dibehenyl Methylamine, Dicocamine, Diethyl Ethanolamine, Diethylhexylamine, Dihydrogenated Tallow Methylamine, Dilinoleamidopropyl Dimethylamine, Dimethicone Copolyolamine, Hydrogenated Ditallowamine, Dimethicone Copolyol Bishydroxyethylamine, Dimethyl Behenamine, Dimethyl Hydrogenated Tallowamine, Avocadamidopropyl Dimethylamine, Dimethyl Myristamine, Dimethyl, Paimitamine, Dimethyl Soyamine, Dimethyl Stearamine, Dimethyl Tallowamine, Dipalmitamine, Disoyamine, Ditallowamidoethyl Hydroxypropylamine, Laurylamine Dipropylenediamine, Linoleamidopropyl Dimethylamine, Hydrogenated Tallowamine, Isostearamidopropyl Dimethylamine, Lauramidopropyl Dimethylamine, Lauraminopropylamine, Oleamine, Olivamidopropyl Dimethylamine, Minkamidopropyl Dimethylamine, Myristamidopropyl Dimethylamine, Oleamidopropyl Dimethylamine, Palmitamidopropyl Diethylamine, Palmitamine, Palmitoyl Methoxytryptamine, PEG-105 Behenyl Propylenediamine, PEG-3 Cocamine, PEG-15 Cocopolyamine, Palmitamidopropyl Dimethylamine, PEG-5 Hydrogenated Tallow Amine, PEG-5 Isodecyloxypropylamine, PEG-6 Oleamine, PEG-12 Palmitamine, PEG-2 Soyamine, PEG-5 Stearamine, PEG-7 Tallow Amine, PEG-3 Tallow Aminopropylamine, PEG-15 Tallow Polyamine, Piroctone Olamine, Poloxamine 304, PPG-2 Cocamine, PPG-2 Hydrogenated Tallowamine, PPG-2 Tallowamine, PPG-3 Tallow Aminopropylamine, Ricinoleamidopropyl Dimethylamine, Sesamidopropyl Dimethylamine, Stearamidoethyl Diethanolamine, Stearamine, Tallamidopropyl Dimethylamine, Soyamine, Soyaminopropylamine, Tallow Amine, Tallowaminopropylamine, Trilaurylamine, Wheat Germamidopropyl Dimethylamine.

Inorganic bases or smaller molecular weight organic bases do not work as well as larger molecular weight bases. Some of them may cause an incompatibility problem between polyethylenimine and salicylic acid. The amount of base used in the composition is dependent on the molecular weight of the base and also the hydrolytic reaction of the corresponding salt. The larger the molecular weight is, the more amount of amine is needed.

Suitable amphoteric surfactants include, but are not limited to, alkyl or alkylamido betaines; and acylamphoglycinates or acylamphoproplonates. The examples of alkyl or alkylamido betaines include, but not limited to, Behenamidopropyl Betaine, Almondamidopropyl Betaine, Canolamidopropyl Betaine, Apricotamidopropyl Betaine, Avocadamidopropyl Betaine, Babassuamidopropyl Betaine, Behenyl Betaine, Capryl/Capramidopropyl Betaine, Coco-Betaine, Cetyl Betaine, Cocamidoethyl Betaine, Decyl Betaine, Cocamidopropyl Betaine, Cocamidopropyl Betaine NI]EA Chloride, Coco/Oleamidopropyl Betaine, Dimethicone Propyl PG-Betaine, Hydrogenated Tallow Betaine, Isostearamidopropyl Betaine, Lauramidopropyl Betaine, Lauryl Betaine, Methacryloyl Ethyl Betaine/Acrylates Copolymer, Milkamidopropyl Betaine, Minkamidopropyl Betaine, Myristamidopropyl Betaine, Myristyl Betaine, Oleamidopropyl Betaine, Oleyl Betaine, Olivamidopropyl Betaine, Palmamidopropyl Betaine, Palmitamidopropyl Betaine, Palm Kernelamidopropyl Betaine, Polytetrafluoroethylene Acetoxypropyl Betaine, Ricinoleamidopropyl Betaine, Sesamidopropyl Betaine, Soyamidopropyl Betaine, Stearamidopropyl Betaine, Stearyl Betaine, Tallowamidopropyl Betaine, Tallow Betaine, Tallow Dihydroxyethyl Betaine, Undecylenamidopropyl Betaine, Wheat Germamidopropyl Betaine.

Examples of acylamphoglycinates and acylamphopropionates include, but not limited to, Caproamphoglycinate, Capryloamphoglycinate, Cocoamphoglycinate, Isostearoamphoglycinate, Lauroamphoglycinate, Myristoamphoglycinate, Oleoamphoglycinate, Stearoamphoglycinate, Tallowamphoglycinate, Undecylenoamphoglycinate, Cocobetainamido Amphopropionate, Cocoamphocarboxyglycinates, Cocoamphopropionate and Cocoamphocarboxypropionate.

In order to control the rheology of the composition, common rheology modifiers can be used to modify the viscosity and rheology. Either non-ionic or anionic polymers as well as cationic polymers are suitable for this purpose. The suitable non-ionic or anionic polymers include, but are not limited to, Carboxymethyl Hydroxyethylcellulose, Cetyl Hydroxyethylcellulose, Ditallow Dimonium Cellulose Sulfate, Ethylcellulose, Cellulose, Cellulose Acetate, Cellulose Acetate Butyrate, Cellulose Acetate Propionate, Cellulose Acetate Proplonate Carboxylate, Cellulose Gum, Hydroxybutyl Methylcellulose, Hydroxyethylcellulose, Methyl Hydroxyethylcellulose, Microcrystalline Cellulose, Hydroxyethyl Ethylcellulose, Hydroxypropylcellulose, Hydroxypropyl Methylcellulose, Hydroxypropyl Methylcellulose Acetate/Succinate, Methylcellulose, Methyl EthylcelluloseNitrocellulose, Nonoxynyl Hydroxyethylcellulose, Cellulose Ester, Acetobutyrate Cellulose, Acetylbutyrylcellulose, Acetylproplonylcellulose, Carboxymethyl Cellulose, Acetate Butanoate Cellulose, 2-Hydroxyethyl Ether Cellulose, 2Hydroxyethyl Ether, Polymer with N,N-Dimethyl-N-2-Propenyl-2-Cellulose, Cellulose, Hexadecyl Hydroxyethyl Cellulose, Hydroxyethylcellulose, Dimethyldiallylammonium Chloride Copolymer, Hydroxyethylcellulose Ethylether, Hydroxypropyl Methylcellulose 2208, Hydroxypropyl Methylcellulose 2906, Hydroxypropyl Methylcellulose 2910, 2Hydroxyethyl 2-(2-Hydroxy-3-

(Trimethylammonio)Propoxy)Ethyl 2-Hydroxy-3 (Trimethylammonio)Propyl Ether, 2-Hydroxyethyl 2-Hydroxy-3-(Trimethylammonio)Propyl Ether Cellulose, 2-Hydroxyethyl 23-Hydroxy-3-(Trimethylammonio)Propyl Ether Cellulose, 2-hydroxyethyl Methyl Ether Cellulose, 2-Hydroxypropyl Ether, Acetate Propanoate Cellulose, Butyrate Acetate Cellulose, Carboxymethyl Ether Cellulose, Carboxymethyl Ether, Sodium Carboxymethyl-2-Hydroxyethyl Ether Cellulose, Cellulose Ethyl Hydroxyethyl Ether, Ethyl Methyl Ether Cellulose, Hexadecyl 2-Hydroxyethyl Ether Cellulose, Hydroxybutyl Methyl Ether Cellulose, Hydroxyethylate, 2-Hydroxypropyl Methyl Ether Cellulose, 2-Hydroxypropyl Methyl Ether, Acetate Hydrogen Butanedloate Cellulose, 2-[2-Hydroxy-3-(Trimethylammonio)Propoxy]Ethyl Ether Cellulose, 2-[2-Hydroxy-3(Trimethylammonio)Propoxy]Ethyl Ether Cellulose, 2-[2-Hydroxy-3Trimethylammonio)propoxy] Ethyl ether Cellulose, Methyl Ether Cellulose, Ethyl Hydroxyethyl Cellulose, Ethyl Methyl Cellulose, H. E. Cellulose, Methyl Hydroxypropyl Cellulose, Carboxymethyl Hydroxypropyl Guar, Cyamopsis Tetragonotoba (Guar) Gum, Hydroxypropyl Guar, Ilex Paraguariensis Leaf Extract, Mate (Ilex Paraguariensis) Extract, Hydroxypropyl Guar, Ilex Paraguariensis, Ilex Paraguariensis Leaf Extract, Cyamopsis Tetragonoloba (Guar) Gum, Extract of Guarana, Extract of Ilex Paraguariensis, Guarana Extract, Guar (Cyamopsis Tetragonoloba) Gum, Carboxymethyl 2-Hydroxypropyl Ether Guar Gum, 2-Hydroxypropyl Ether Guar Gum, 2-Hydroxy-3-(Trimethylammonio)Propyl Ether Guar Gum, Sodium Carboxymethyl Cellulose, Calcium Cellulose Glycolate, Sodium Cellulose Sulfate, Sodium Carboxymethyl Hydroxyethylcellulose, Calcium Carboxymethyl Cellulose.

Suitable cationic polymers include, but are not limited to, Nitrocellulose Quaternary Ammonium Compounds, Coco Alkyl (2,3-Dihydroxypropyl)Dimethyl, O-[2-Hydroxy-3 (trimethylammonio)propyl] Guar Gum Chloride, Guar Hydroxypropyltrimonium Chloride, Hydroxypropyltrimonium Chloride, 2-hydroxypropyl 2-hydroxy-3-(trimethylammonio)propyl ether Guar Gum Chloride, Polyquaternium-2, Polyquaternium-4, Polyquaternium-6, Polyquaternium-7, Polyquaternium-10, Polyquaternium-11, Polyquaternium-22, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein, PG-Hydroxyethylcellulose Cocodimonium Chloride, PGHydroxyethyicellulose Lauryldimonium Chloride, PG-Hydroxyethylcellulose Stearyl dimonium Chloride, O-[2-Hydroxy-3-(trimethylammonio)propyl] Hydroxyethylcellulose Chloride. By changing the different polymers, compositions of variable viscosity & rheology can be prepared.

Other common cosmetic ingredients can include preservatives, color, and fragrance. However, they do not play functional roles for conditioning of hair and scalp.

The treatment composition has been designed to repair damaged hair, especially from split-ends and also to treat daily problems of the scalp. The composition is designed to be preferably used twice a week and will facilitate the elimination of split-ends and transform damaged hair into healthy hair. For normal hair, it helps protect hair from damage and balances the moisture of the hair leaving the hair healthier looking. At the same time, it also helps prevent itchiness of the scalp and helps prevent dandruff from forming.

The invention is further illustrated by the following exemplar formulations, which are intended as illustrations only and not as a limitation to the scope of the invention. The thermal and physical stabilities (compatibility of PEI and anti-dandruff agent) have been tested at both ambient temperature and 40° C. for three (3) months.

EXAMPLE 1

| Phase I | |
|---|---|
| Water (Aqua) | 35.0% |
| Oleamidopropyl Dimethylamine | 3.4% |
| Salicylic Acid | 3.0% |
| Oleth-20 | 1.1% |
| Hexylene Glycol | 1.0% |
| Phase II | |
| Water (Aqua) | 40.0% |
| PEI-1 000 | 0.55% |
| Lactic acid | 0.67% |
| Menthol | 0.25% |
| Hydroxyethylcellulose | 0.20% |
| Behenamidopropyl Betaine | 2.1% |
| Fragrance (Parfum) | q.s. |
| Preservative | q.s. |
| Color | q.s. |
| Water (Aqua) | to 100% |

EXAMPLE 2

| Phase I | |
|---|---|
| Water (Aqua) | 35.0% |
| Behenamidopropyl Dimethylamine | 4.2% |
| Salicylic Acid | 3.5% |
| Oleth-20 | 0.7% |
| Phase II | |
| Water (Aqua) | 40.0% |
| Propylene Glycol | 1.0% |
| PEI-700 | 1.50% |
| Benzoic Acid | 1.4% |
| Polyquatemium-10 | 0.20% |
| Cocamidopropyl Betaine | 2.00% |
| Fragrance (Parfum) | q.s. |
| Preservative | q.s. |
| Color | q.s. |
| Water (Aqua) | to 100% |

EXAMPLE 3

| Phase I | |
|---|---|
| Water (Aqua) | 35.0% |
| Oleamidopropyl Dimethylamine | 1.65% |
| Salicylic Acid | 1.8% |
| Oleth-5 | 0.8% |
| Hexylene Glycol | 1.0% |
| Phase II | |
| Water (Aqua) | 40.0% |
| PFI- 1 500 | 1.50% |
| Lactic Acid | 1.40% |
| Methyl Hydroxyethylcellulose | 0.20% |
| Lauramidopropyl Betaine | 2.50% |
| Fragrance (Parfum) | q.s. |
| Preservative | q.s. |

EXAMPLE 4

Phase I

| | |
|---|---|
| Water (Aqua) | 35.0% |
| Cocamidopropyl Dimethylamine | 0.6% |
| Salicylic Acid | 0.0% |
| Oleth-20 | 1.2% |
| Butylene Glycol | 1.0% |

Phase II

| | |
|---|---|
| Water (Aqua) | 40.0% |
| PEI-1400 | 4.75% |
| Lactic acid | 4.67% |
| Hydroxypropyl Guar | 0.20% |
| Oleamidopropyl Betaine | 2.50% |
| Fragrance (Parfum) | q.s. |
| Preservative | q.s. |
| Color | q.s. |
| Water (Aqua) | to 100% |

EXAMPLE 5

Phase I

| | |
|---|---|
| Water (Aqua) | 35.0% |
| PEG-3 Cocamine | 1.1% |
| Salicylic Acid | 1.0% |
| Oleth-5 | 1.3% |
| Glycerin | 1.0% |

Phase II

| | |
|---|---|
| Water (Aqua) | 40.0% |
| PEI-1750 | 4.75% |
| Benzoic Acid | 5.67% |
| Guar Hydroxypropyltrimonium Chloride, | 0.20% |
| Soyamidopropyl Betaine | 2.10% |
| Fragrance (Parfum) | q.s. |
| Preservative | q.s. |
| Color | q.s. |
| Water (Aqua) | to 100% |

EXAMPLE 6

Phase I

| | |
|---|---|
| Water (Aqua) | 35.0% |
| Ricinoleamidopropyl Dimethylamine | 0.9% |
| Salicylic Acid | 0.8% |
| Oleth-10 | 1.1% |
| Butylene Glycol | 1.0% |

Phase II

| | |
|---|---|
| Water (Aqua) | 40.0% |
| PEI-2500 | 0.75% |
| Lactic acid | 0.67% |
| Polyquaternium-7 | 0.20% |
| Palmitamidopropyl Betaine | 1.90% |
| Fragrance (Parfum) | q.s. |
| Preservative | q.s. |
| Color | q.s. |
| Water (Aqua) | to 100% |

EXAMPLE 7

Phase I

| | |
|---|---|
| PEG-4 | 41.0% |
| Soyaminopropylamine | 4.1% |
| Salicylic Acid | 3.0% |
| Oleth-20 | 1.1% |

Phase II

| | |
|---|---|
| Propylene Glycol | 30.0% |
| PEI- 1400 | 0.75% |
| Benzoic Acid | 0.67% |
| Acrylates/Aminoacrylates/C10–30 Alkyl PEG-20 Itaconate Copolymer | 1.20% |
| Cocoamphoglycinate | 2.05% |
| Fragrance (Parfum) | q.s. |
| Preservative | q.s. |
| Color | q.s. |
| Propylene Glycol | to 100% |

EXAMPLE 8

Phase I

| | |
|---|---|
| PEG-6 | 35.6% |
| Oleamidopropyl Dimethylamine | 2.5% |
| Salicylic Acid | 1.6% |
| Oleth-20 | 1.1% |

Phase II

| | |
|---|---|
| Propylene Glycol | 30.0% |
| PEI-1500 | 2.50% |
| Lactic acid | 2.20% |
| Hydroxyethylcellulose Cocodimonium Chloride | 0.20% |
| Cocoamphopropio-nate | 2.50% |
| Fragrance (Parfum) | q.s. |
| Preservative | q.s. |
| Color | q.s. |
| Propylene Glycol | to 100% |

EXAMPLE 9

Phase I

| | |
|---|---|
| PEG-8 | 31.5% |
| PEG-5 Isodecyloxypropylamine | 4.1% |
| Salicylic Acid | 3.0% |
| Oleth-20 | 1.1% |

Phase II

| | |
|---|---|
| Propylene Glycol | 30.0% |
| PEI-1750 | 4.75% |
| Benzoic Acid | 5.67% |
| Eucalyptus | 0.25% |
| Carboxymethyl Hydroxyethylcellulose | 0.20% |
| Isostearamidopropyl Betaine | 2.10% |
| Fragrance (Parfum) | q.s. |
| Preservative | q.s. |
| Color | q.s. |
| Propylene Glycol | to 100% |

EXAMPLE 10

| Phase I | |
|---|---|
| PEG-4 | 38.2.0% |
| Isostearamidopropyl Dimethylamine | 4.3% |
| Salicylic Acid | 3.2% |
| Oleth-5 | 0.5% |
| Phase II | |
| Propylene Glycol | 30.0% |
| PEI- 1400 | 3.65% |
| Benzoic Acid | 4.87% |
| Menthol | 0.25% |
| Paimitamidopropyltrimonium Chloride | 1.20% |
| Polyquaternium- 11 | 0.20% |
| Myristamidopropyl Betaine | 2.40% |
| Fragrance (Parfum) | q.s. |
| Preservative | q.s. |
| Colors | q.s. |
| Propylene Glycol | to 100% |

EXAMPLE 11

| Water (Aqua) | to 100% |
|---|---|
| Oleth-10 | 1.1% |
| Butylene Glycol | 1.0% |
| PEI-1750 | 1.75% |
| Lactic acid | 1.37% |
| Polyquaternium-7 | 0.20% |
| Palmitamidopropyl Betaine | 3.9% |
| Zinc Pyrithione | 2.00% |
| Fragrance (Parfum) | q.s. |
| Preservative | q.s. |
| Color | q.s. |

Examples 1–6 and 11 are aqueous formulations and examples 7–10 are anhydrous formulations. The anhydrous formulations have self-heating action whenever they are applied on the wet hair.

The composition is obtained by preparing two-separated phases at room temperature and then mixing them together for a sufficient time, preferably for one (1) hour. The fragrance, preservatives and colors are added in afterwards. It is important that the pH of the two phases be similar and preferably substantially similar. If the difference of pH in two phases is larger than two pH units, precipitation may occur.

The following is intended to literally define the scope of the present invention, and all equivalents are intended to be covered as well.

What is claimed is:

1. A method of treating the hair and scalp, the method comprising the steps of:
    (a) placing a composition on the hair,
        wherein said composition comprises:
            (i) about 0.1 to 7.0 wt % of salicylic acid,
            (ii) about 0.1 to 8.0 wt % of a at least one polyethylenimine, and
            (iii) about 0.01 to 12.0 wt % of at least one amphoteric surfactant,
        wherein the ratio of ingredient (i) to ingredient (ii) is about 1:0.05 to 1:50,
    (b) wherein the composition treats the hair and the scalp, and
    (c) shampooing the hair to remove at least a portion of said composition therefrom.

\* \* \* \* \*